(12) United States Patent
Mizukami et al.

(10) Patent No.: US 6,911,563 B2
(45) Date of Patent: Jun. 28, 2005

(54) REACTION METHOD UTILIZING DIAPHRAM TYPE CATALYST AND APPARATUS THEREFOR

(75) Inventors: Fujio Mizukami, Sendai (JP); Shuichi Niwa, Sendai (JP); Makoto Toba, Tsukuba (JP); Naotsugu Itoh, Tsukuba (JP); Tomonari Saito, Tsukuba (JP); Takemi Nanba, Tsukuba (JP); Hiroshi Shoji, Ichihara (JP); Kazuhiko Haba, Ichihara (JP)

(73) Assignees: National Institute of Advanced Industrial Science, Tokyo (JP); NOK Corporation, Tokyo (JP)

( * ) Notice: Subject to any disclaimer, the term of this patent is extended or adjusted under 35 U.S.C. 154(b) by 0 days.

(21) Appl. No.: 10/451,624

(22) PCT Filed: Dec. 27, 2001

(86) PCT No.: PCT/JP01/11542

§ 371 (c)(1),
(2), (4) Date: Dec. 10, 2003

(87) PCT Pub. No.: WO02/055465

PCT Pub. Date: Jul. 18, 2002

(65) Prior Publication Data

US 2004/0110995 A1 Jun. 10, 2004

(30) Foreign Application Priority Data

Jan. 5, 2001 (JP) ........................ 2001-000403
Mar. 26, 2001 (JP) ........................ 2001-088282

(51) Int. Cl.$^7$ ............................................ C07L 37/00
(52) U.S. Cl. ........................ 568/802; 546/290; 549/533; 568/376; 568/401; 568/476; 568/735; 568/836
(58) Field of Search ................. 568/802, 376, 568/401, 476, 735, 836, 771; 546/290; 549/533

(56) References Cited

FOREIGN PATENT DOCUMENTS

| | | |
|---|---|---|
| JP | 44-11362 | 5/1969 |
| JP | 53-001177 | 1/1978 |
| JP | 60-051125 | 3/1985 |
| JP | 63-011685 | 1/1988 |
| JP | 03-122296 | 5/1991 |
| JP | 04-364144 | 12/1992 |
| JP | 05-238961 | 9/1993 |
| JP | 05-295578 | 11/1993 |
| JP | 06-001738 | 1/1994 |
| JP | 06-057470 | 3/1994 |
| JP | 06-072919 | 3/1994 |
| JP | 07-069950 | 3/1995 |
| JP | 11-300182 | 11/1999 |
| WO | WO97/28142 | 8/1997 |

OTHER PUBLICATIONS

Niwa et al, SCIENCE, vol. 295, Jan. 4, 2002, pp. 105–107, A One–Step Conversion of Benzene to Phenol with a Palladium . . .
Kharitonov et al, Appl. Catal. A 98, 1993, pp. 33–43, Ferrisilicate analogs of ZSM–5 zeolite as catalysts for . . .
Yamanaka et al, Appl. Catal. A 171, 1998, pp. 309–314, One–Step synthesis of propylene oxide catalysed by the . . .

Primary Examiner—Michael L. Shippen
(74) Attorney, Agent, or Firm—Jacobson Holman PLLC

(57) ABSTRACT

A method for carrying out a reaction of one substance capable of being activated by a catalyst with another substance capable of reacting with said one substance activated, characterized in that the substance capable of being activated is activated by passing the substance through a diaphragm type catalyst and the reaction is thus performed in one reaction step; a method for producing an aromatic alcohol utilizing the above method; and a reaction apparatus suitable for these reactions. In the method, one substance is activated by passing through a diaphragm type catalyst and an objective reaction is carried out by using the activated substance, and the reaction can be performed in one reaction step and with safety. Moreover, the contact of the above activated substance with a compound to be reacted therewith can be freely controlled, and therefore, over-reaction can be prevented and an objective product can be produced in high yield. The method is thus markedly advantageous from an economical view point as a commercial process for producing oxygen-containing organic compounds such as an aromatic alcohol, a ketone, an aldehyde, a carboxylic acid and an epoxide.

29 Claims, 5 Drawing Sheets

REACTION METHOD UTILIZING DIAPHRAM TYPE CATALYST AND APPARATUS THEREFOR

This is a nationalization of PCT/JP01/11542 filed Dec. 27, 2001 and published in Japanese.

TECHNICAL FIELD

The present invention relates to a reaction method utilizing a substance to be activated by the action of a catalyst, a method of producing aromatic alcohols utilizing this method, and a reaction apparatus for these methods.

BACKGROUND ART

An oxygen oxidation reaction which oxidizes a hydrocarbon with oxygen or air in the presence of an oxidation catalyst plays a highly important role in the organic chemical industry. Examples of an oxygen-containing organic compound obtained by such a reaction include ketones such as acetone, cyclohexanone, and cyclopentanone; carboxylic acids such as terephthalic acid, phthalic anhydride, and maleic anhydride; and alkylene oxides such as ethylene oxide.

The oxygen-containing organic compounds include aromatic alcohols, many of which are important as a basic chemical product used in the organic chemical industry. Of these, phenol and cresol are particularly important chemical products. Phenol or cresol is subjected to a polycondensation reaction with formaldehyde to produce a phenol resin or cresol resin, for example. These resins are broadly used as a coating material, lacquer, or resin raw material for compression molding or foam molding. Phenol is used as a raw material of bisphenol A or bisphenol F which is important as a raw material of an epoxy resin. Cyclohexanol obtained by hydrogenating phenol is used for producing ε-caprolactam which is a raw material for nylon.

Roughly two methods for producing phenol which is important among aromatic alcohols are known in the art. In one method, benzene or alkylbenzene is chemically oxidized to synthesize phenol. In the other method, tar which is obtained by dry distillation of coal is fractionated or extracted to produce phenol. Phenol produced utilizing the latter method has a low purity due to many impurities. Accordingly, an indirect method which oxidizes alkylbenzene is mainly utilized at present.

As a method for industrial production of phenol based on the above oxidation method, a "direct oxidation method" which partially oxidizes benzene directly is the most ideal. Since it is difficult to control the reaction when the "direct oxidation method" is utilized, phenol produced by oxidizing benzene is further oxidized. Therefore, the method has not been practical until now.

Of the indirect methods for producing phenol, a cumene method is the most popular. The cumene method comprises synthesizing cumene by reacting propylene with benzene, oxidizing cumene with air using a cobalt salt catalyst, for example, to produce cumene hydroperoxide, and decomposing the resulting cumene hydroperoxide into phenol and acetone by the action of an acid catalyst. This method is highly excellent due to a high selectivity of phenol. However, acetone is also produced with the same molar ratio as phenol. Therefore, the cost of phenol fluctuates in accordance with the acetone demand.

Some "direct oxidation methods" have recently been proposed. For example, a paper of G. I. Panov (see Appl. Catal. A., 98, 33 (1993)) discloses a method for directly oxidizing benzene using nitrous oxide as an oxidizer to obtain phenol. A problem with this method is in the difficulty of synthesizing nitrous oxide. Japanese Patent Applications Laid-open No. 6-1738 and No. 7-69950 propose a method for oxidizing benzene using hydrogen peroxide as an oxygen source in the presence of various catalysts such as iron or a noble metal supported on a carrier, zeolite, and heteropolyacid. This method is environmentally friendly since only water is the bi-product. However, a huge amount of expensive hydrogen peroxide is needed. A paper of Yamanaka, Otsuka, et al. (see Appl. Catal. A., 171, 309 (1998)) discloses that benzene is oxidized using oxygen gas in the presence of an europium catalyst carried on titania. In this method, the manner of handling the europium catalyst is complicated, and the yield of phenol is only 2–4%.

Thus, since no economically satisfactory process for producing phenol by directly oxidizing benzene has been developed, phenol is usually produced by the indirect oxidation method. Similar circumstances can be found in the case of producing propylene oxide by oxidizing propylene.

However, the indirect oxidation method involves many complicated reaction steps and production of unnecessary bi-products. Therefore, development of the direct oxidation method for directly oxidizing a hydrocarbon has been desired.

Conventionally, as the direct oxidation method for producing an oxygen-containing organic compound, a method comprising first mixing a hydrocarbon as a raw material with a gas such as oxygen and then circulating the mixture in a fixed bed circulation reaction apparatus filled with a solid catalyst has been known. This method, however, has a problem of an extremely low reaction yield.

One reason for the low reaction yield is the low selectivity of the target compound. Since the oxygen-containing compound produced by the reaction has a decreased molecular ionization potential, the compound is oxidized more easily than the raw material hydrocarbon. Therefore, the target product is successively overreacted (oxidized), which leads to a decreased selectivity of the product. In order to control this overreaction, reaction conditions in which the concentration of raw materials greatly exceeds the concentration of the product must be employed. This type of reaction in which a flammable material is reacted with oxygen inducing combustion (a combustion promoter) involves an explosion risk. To avoid the explosion risk, the product cannot but be produced at a low reaction yield under low concentration conditions. These are the reasons for the low reaction yield.

Published Japanese Translation of PCT Publication for Patent Application No. 11-510817 discloses a gaseous phase oxidation reaction of propylene into propylene oxide in the presence of a silver catalyst carried on a solid carrier, for example. According to examples specifically disclosed, the raw material propylene concentration in a gas mixture introduced into a reactor is as low as 10% or less, and the conversion rate of propylene is as low as 3–5%.

As described above, in a system in which oxygen, a raw material hydrocarbon, and a product coexist, it is essentially difficult to produce the target product at a high yield while avoiding an explosion risk and preventing successive oxidation reactions.

The use of a diaphragm type reactor called a membrane reactor in a gaseous phase oxidation reaction using a hydrocarbon as a raw material has been reported. For example, Japanese Patent Application Laid-open No. 5-238961 discloses that the membrane reactor can be utilized to produce $C_2$ hydrocarbons based on an oxidative coupling reaction of methane.

The diaphragm type catalyst used in this Patent Application is a complex oxide having a high oxygen ionic mobility and mixing conductivity. This is an ion conductor involved in the reaction which converts oxygen introduced from one side of the diaphragm into oxygen ion $O^{2-}$ to circulate and discharges the oxygen ion to the other side of the diaphragm. However, since oxygen moves or is supplied slowly in the ion conductor, it is difficult to achieve a reaction speed applicable for the actual production of chemicals in the organic chemical industry.

Japanese Patent Application Laid-open No. 5-194281 discloses a method for a catalytic dehydration reaction of a saturated hydrocarbon using a hydrogen permeation membrane and a dehydration catalyst in combination. Utilizing this method, hydrogen produced by a dehydration reaction permeates through the membrane to be discharged from the reaction system. As a result, the chemical equilibrium in the system is shifted to the dehydration reaction side, whereby a conversion rate above an equilibrium conversion rate is obtained.

The products obtained by the above methods using the diaphragm type reactor are hydrocarbon compounds, not oxygen-containing organic compounds. Specifically, a method for producing an oxygen-containing organic compound using the diaphragm type reactor has not been proposed so far.

Therefore, an object of the present invention to provide a method for reacting a substance to be activated by the action of a catalyst such as oxygen or hydrogen with a substance to be reacted with the activated substance such as a hydrocarbon to obtain a product at a high yield while avoiding an explosion risk and ensuring safety.

DISCLOSURE OF THE INVENTION

The present inventors have conducted extensive studies for achieving the above object, and found that a target product can be obtained at a high yield with safety by activating a substance to be activated using a membranous diaphragm type catalyst and reacting the activated substance with a substance to be reacted with the activated substance. This finding has led to the completion of the present invention.

Specifically, an object of the present invention is to provide a method for reacting a substance to be activated by the action of a catalyst with a substance to be reacted with the activated substance, the method comprising activating the substance to be activated while permeating through a diaphragm type catalyst, thereby effecting the reaction in one step.

Another object of the present invention is to provide the above method comprising providing a reactor with a plurality of adjacent chambers partitioned by the diaphragm type catalyst that can activate a substance permeating therethrough, causing a gas of the substance to be activated by the diaphragm type catalyst to circulate in one of the chambers, causing the compound to be reacted with the activated substance to circulate in the other chamber, activating the substance to be activated while permeating through the diaphragm type catalyst, and reacting the activated substance with the compound to be reacted with the activated substance.

Still another object of the present invention is to provide a method for producing an aromatic alcohol by reacting oxygen, hydrogen, and an aromatic hydrocarbon in one step, wherein hydrogen activated while permeating through a diaphragm type catalyst is reacted with an aromatic hydrocarbon and oxygen.

Yet another object of the present invention is to provide the above method, wherein the reaction is conducted in a reactor partitioned by a diaphragm type catalyst into a plurality of adjacent chambers, one of the chambers being designed to cause hydrogen to circulate and the other chamber being designed to cause an aromatic hydrocarbon and oxygen to circulate, wherein hydrogen is activated while permeating through the diaphragm type catalyst and the activated hydrogen is reacted with the aromatic hydrocarbon and oxygen.

A further object of the present invention is to provide a reaction apparatus having a reactor partitioned by a diaphragm type catalyst into a plurality of adjacent chambers, one of the chambers being designed to cause a gas of a substance to be activated while permeating through the diaphragm type catalyst to circulate and the other chamber being designed to cause a compound to be reacted with the activated substance to circulate, wherein the substance to be activated is activated while permeating through the diaphragm type catalyst and the activated substance is reacted with the compound to be reacted with the activated substance.

Figure 1:
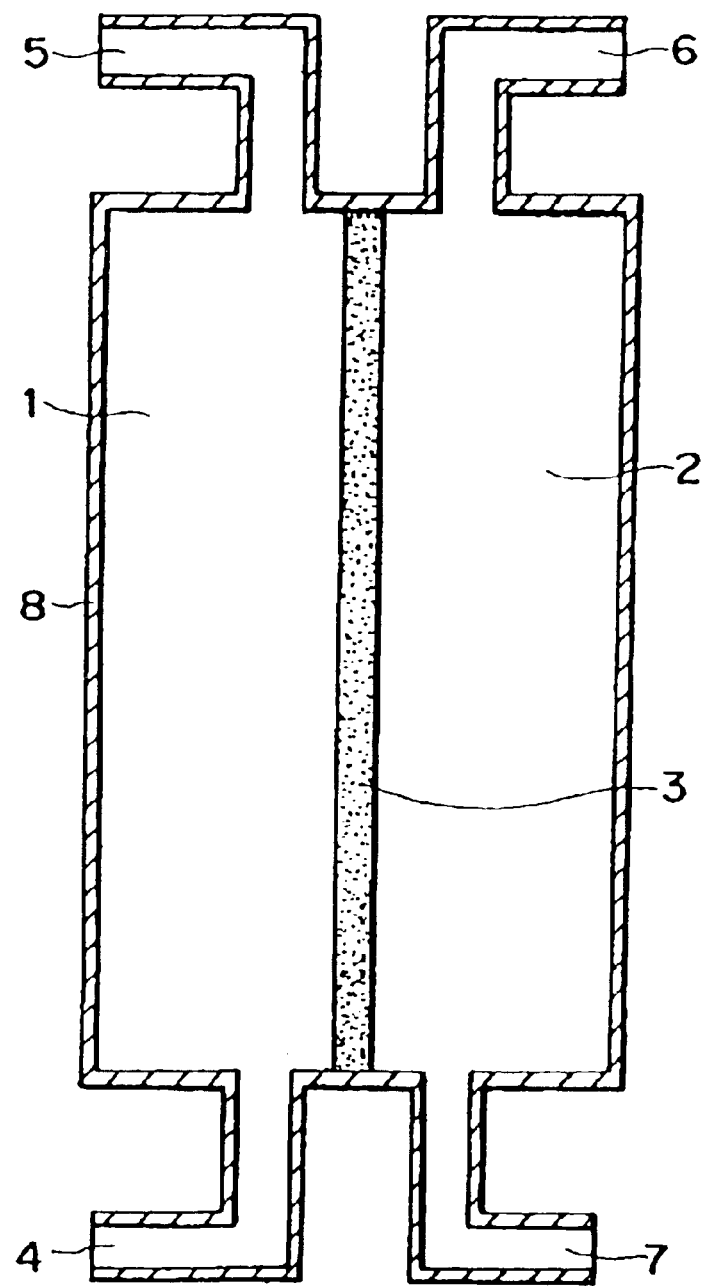
FIG. 1 is a cross-sectional view schematically showing an embodiment of the diaphragm type catalyst reaction apparatus of the present invention.

1 Reaction compound residence section
2 Activation substance circulation section
3 Diaphragm type catalyst
4 Reaction compound inlet port
5 Reaction compound outlet port
6 Activation substance inlet port
7 Activation substance outlet port
8 Reactor (external cylinder)
9 Internal cylinder
10 Oxygen gas volatilization apparatus (bubbler)
11 Level gauge

BEST MODE FOR CARRYING OUT THE INVENTION

In this specification, the "diaphragm type catalyst" refers to a membranous catalyst which can partition a reactor into two or more reaction zones. The present invention basically relates to a reaction in which one substance involved in the reaction which is present in one of the two reaction zones partitioned by the diaphragm type catalyst is activated while permeating through the catalyst and reacted with a compound to be reacted which is present in the other reaction chamber, for example. Use of a plurality of the diaphragm type catalysts further increases efficiency in the reaction and enables a scale-up of the reaction and the like.

Examples of the reaction utilizing the diaphragm type catalyst according to the present invention include a reaction (hereinafter referred to as "first embodiment reaction") in which the substance to be activated (hereinafter referred to as "activation substance") is oxygen, the compound to be reacted with the activated substance (hereinafter referred to as "reaction compound") is a hydrocarbon, and the compound obtained by the reaction (hereinafter referred to as "product") is an oxygen-containing organic compound, and a reaction (hereinafter referred to as "second embodiment reaction") in which the activation substance is hydrogen, the reaction compounds are a hydrocarbon and oxygen, and the product is an oxygen-containing organic compound.

Specific examples of the first embodiment reaction include oxidation reactions for oxidizing a raw material hydrocarbon using activated oxygen to produce oxygen-containing organic compounds such as an alkylene oxide using an olefin hydrocarbon as a raw material; ketone using an olefin hydrocarbon or cyclic hydrocarbon as a raw material; aldehyde using an olefin hydrocarbon as a raw material; and carboxylic acid using a paraffin hydrocarbon, olefin hydrocarbon, or aromatic hydrocarbon as a raw material.

Specific examples of the second embodiment reaction include reactions of a hydrocarbon and oxygen as raw materials with activated hydrogen to produce an oxygen-containing organic compound such as an aldehyde, ketone, alkylene oxide, and aromatic alcohol using an olefin such as propylene or butene as a raw material.

A diaphragm type catalyst is an essential component of the present invention. A substance is activated while permeating through the diaphragm type catalyst. The diaphragm type catalyst is a porous membrane of metal or alloy which is a catalytically active component or a membranous porous material carrying the catalytically active component thereon. The specific diaphragm type catalysts include, for example:

(A) a metal membrane,
(B) an alloy membrane,
(C) a noble metal carried on a metal oxide porous membrane, and
(D) a transition metal oxide or lanthanide oxide carried on a metal oxide porous membrane.

A metal, alloy, noble metal, and transition metal oxide or lanthanide oxide are catalytically active components respectively contained in (A), (B), (C), and (D).

As the metal membrane (A), a metal membrane formed from a metal selected from a group consisting of palladium, niobium, tantalum, and vanadium can be given, for example. In addition, a metal membrane formed by applying palladium to a metal membrane formed from a metal selected from a group consisting of niobium, tantalum, and vanadium may also be used.

As the alloy membrane (B), an alloy membrane formed from an alloy of one or more elements selected from a group consisting of first-row transition metals, second-row transition metals, third-row transition metals, lanthanides, and actinides and a metal selected from a group consisting of palladium, niobium, tantalum, and vanadium can be given, for example. In addition, an alloy membrane formed from an alloy of one or more elements selected from a group consisting of yttrium, cerium, silver, nickel, and titanium and a metal selected from a group consisting of palladium, niobium, tantalum, and vanadium may also be used.

The first-row transition metals, second-row transition metals, and third-row transition metals respectively refer to elements of groups 4A–8A in the fourth period of the periodic table, elements of groups 4A–8A in the fifth period of the periodic table, and elements of groups 4A–8A in the sixth period of the periodic table. The lanthanides and actinides respectively refer to elements of the lanthanide series in the periodic table and elements of the actinide series in the periodic table.

The metal and alloy respectively contained in (A) and (B) may be formed as a porous membrane, or carried on a membrane such as a metal oxide porous membrane described later.

As the noble metal (C) carried on the metal oxide porous membrane, a noble metal selected from a group consisting of silver, gold, platinum, and palladium can be given.

As the transition metal oxide (D) carried on the metal oxide porous membrane, an oxide of a transition metal selected from a group consisting of chromium, manganese, iron, cobalt, nickel, osmium, ruthenium, vanadium, molybdenum, tungsten, and bismuth can be given. As the lanthanide oxide (D) carried on the metal oxide porous membrane, an oxide of an element selected from a group consisting of cerium, lanthanum, and samarium can be given.

There are no limitations to the metal oxide porous material used in (C) and (D) inasmuch as the material can allow the catalytically active component to be uniformly dispersed and carried and is useful as a carrier of an oxidation reaction catalyst or the like. Specific examples of said material include a porous material of a metal oxide selected from a group consisting of silica, alumina, titania, and zirconia, a porous material of a composite material formed from two or more of these four metal oxides, and a porous material of zeolite.

In order to appropriately control or reduce the gas permeability, a porous membrane formed by causing silica, alumina, titania, zirconia, zeolite, or the like to be carried on a porous ceramic membrane using a method such as dip coating, spray coating, spin coating, or hydrothermal synthesis may be used.

The metal oxide porous material is basically membranous. However, porous materials of various forms may be used without limitation inasmuch as a gaseous reaction component as a raw material can permeate through the porous material. A pore diameter of the porous material is selected based on the type and conditions of the target reaction. Generally, the pore diameter is 0.5 nm to 10 $\mu$m, and preferably 0.5 nm to 1 $\mu$m. An applicable specific surface area of the porous material is generally 0.5–1,000 m$^2$/g. An applicable membrane thickness of the porous material is 50 $\mu$m to 5 mm. The thickness is preferably 100–500 $\mu$m from the viewpoint of mechanical strength and permeation resistance.

The pore diameter and the specific surface area can be controlled based on the conditions when producing the metal oxide porous material or preparing the catalyst, and are appropriately selected in accordance with the type of reaction.

The metal oxide porous membrane is suitably used in the form of a tube or plate. The porous membrane of such a form can be obtained by using a method disclosed in Japanese Patent Publication No. 5-66343 (Japanese Patent No. 1850556), for example.

The type of the catalytically active component carried on this metal oxide porous membrane is selected according to the type of target reaction. For example, the porous membrane can carry a metal compound such as molybdenum or bismuth to produce an aldehyde, a metal compound such as vanadium to produce a carboxylic acid, or a metal compound such as silver to produce an alkylene oxide.

Examples of a method for causing the catalytically active component to be carried on the metal oxide porous material include methods commonly adopted for preparation of an oxidation reaction catalyst such as an impregnation method, precipitation method, ion-exchange method, vapor deposition method, and hydrothermal synthesis method. In addition, a CVD (chemical vapor deposition) method, PVD (physical vapor deposition) method, dip coating, spray coating, spin coating, and the like are applicable. The amount of the catalytically active component carried on this metal oxide porous membrane is appropriately determined according to the type of the aromatic hydrocarbon and reaction conditions.

There are no limitations to the method of carrying out the present invention inasmuch as an activation substance such as oxygen or hydrogen involved in the reaction is activated while permeating through the diaphragm type catalyst selected from the above (A)–(D) and reacted with a reaction compound such as a hydrocarbon or a mixture of a hydrocarbon and oxygen, for example. A reaction diluent such as nitrogen, steam, helium, carbon dioxide, or methane may be used, as required.

Some examples of a reactor which is advantageously used in the embodiments of the present invention (hereinafter may be referred to as "diaphragm type reactor") will be given. The embodiments of the present invention will be described in more detail by way of these examples, which should not be construed as limiting the present invention.

FIG. 1 is a cross-sectional view schematically showing a diaphragm type catalyst reaction apparatus of the present invention. In FIG. 1, 1 indicates a reaction compound residence section, 2 indicates an activation substance circulation section, 3 indicates a diaphragm type catalyst, 4 indicates a reaction compound inlet port, 5 indicates a reaction compound outlet port, 6 indicates an activation substance inlet port, 7 indicates an activation substance outlet port, and 8 indicates a reactor. In the reaction apparatus shown in FIG. 1, the reactor is partitioned into the reaction compound residence section 1 and the activation substance circulation section 2 by one plane diaphragm type catalyst 3. In the reactor shown in FIG. 1, an activation substance and a reaction compound enter in the reactor in mutually opposite directions and countercurrently flow.

Figure 2:
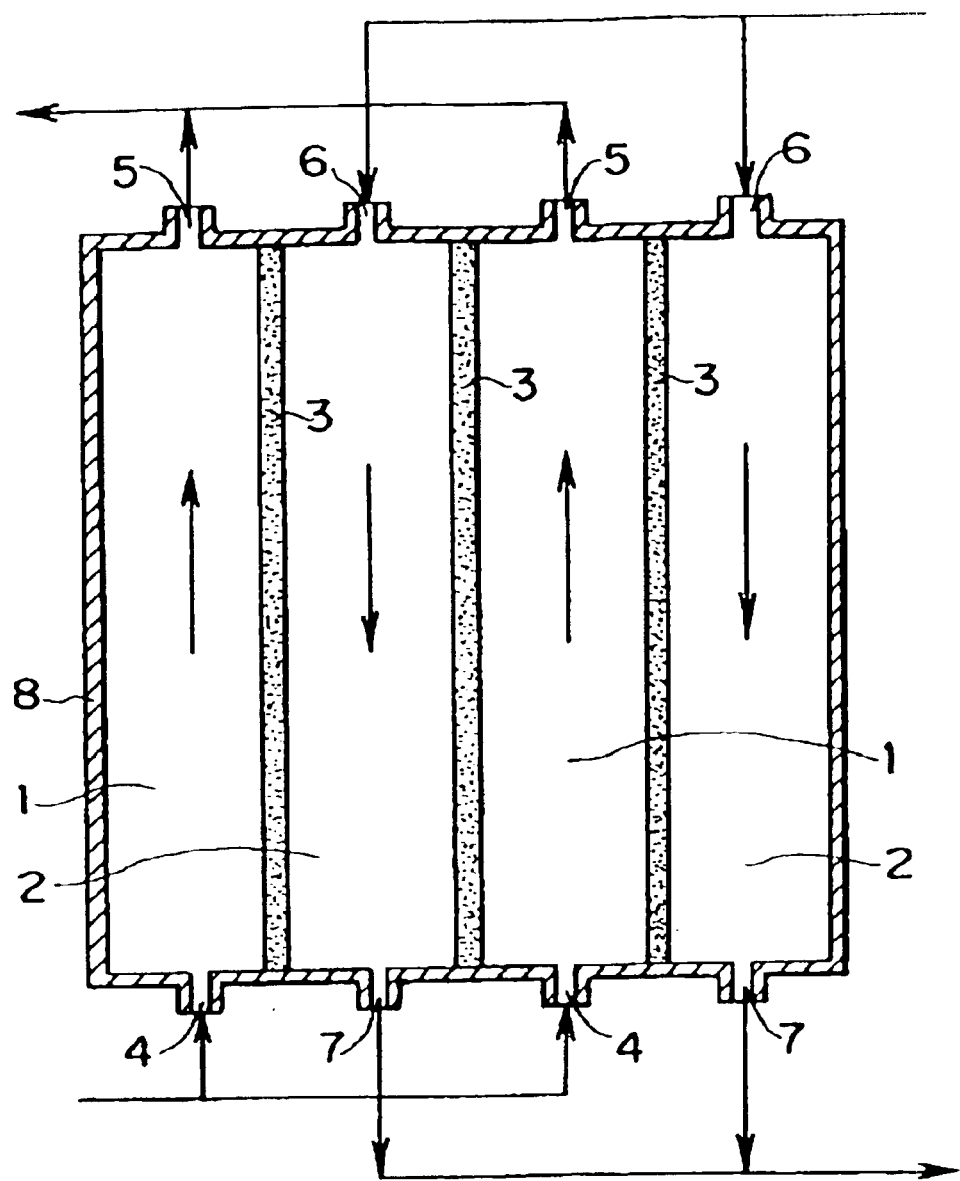
FIG. 2 is a cross-sectional view schematically showing another embodiment of the diaphragm type catalyst reaction apparatus of the present invention.

FIG. 2 is a view showing another reaction apparatus of the present invention. The reaction apparatus of this embodiment is formed by alternately arranging a plurality of the reaction compound residence sections 1 and a plurality of the activation substance circulation section 2. This apparatus is useful for a scaled-up reaction through the diaphragm type catalyst 3, for example. The apparatus is partitioned into four chambers in FIG. 2. However, there are no restrictions on the number of partitions. If an odd number of the diaphragm type catalysts 3 is used, the reactor is partitioned into an even number (one more than the odd number) of chambers.

Figure 3:
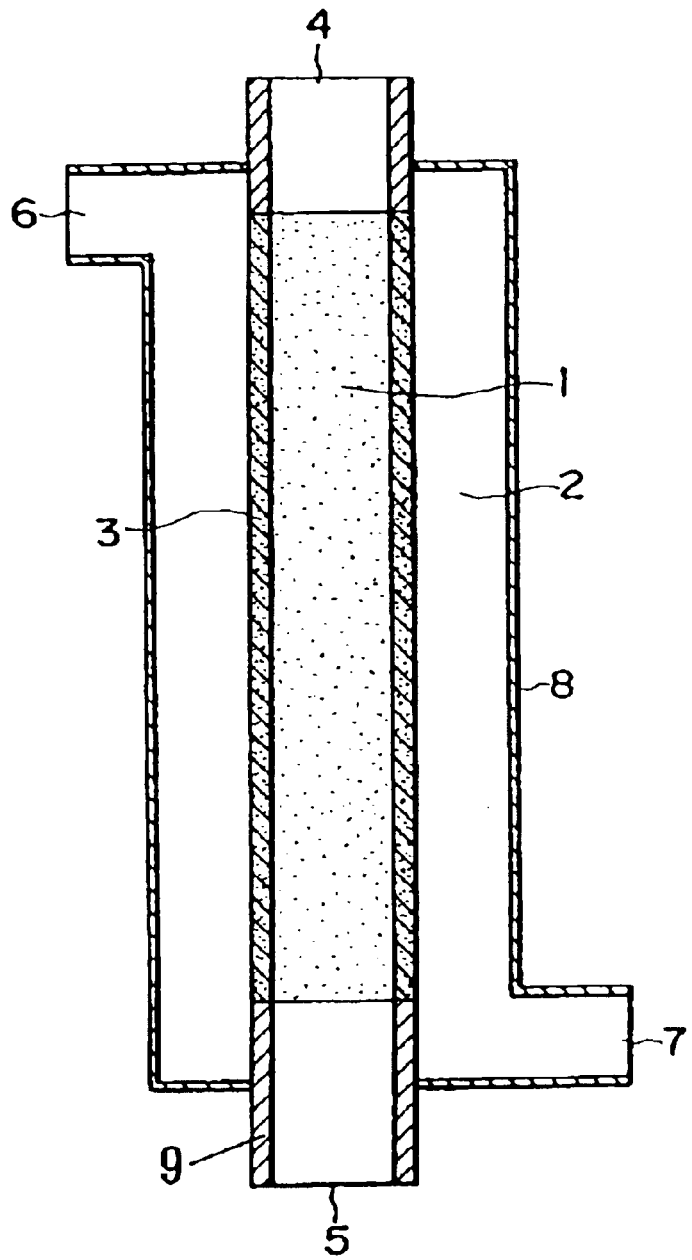
FIG. 3 is a cross-sectional view schematically showing still another embodiment of the diaphragm type catalyst reaction apparatus of the present invention.

FIG. 3 is a view showing still another reaction apparatus of the present invention. The reaction apparatus of this embodiment utilizes the cylindrical diaphragm type catalyst 3, wherein an inner space of an internal cylinder 9 partially or entirely constituted by the diaphragm type catalyst 3 functions as the reaction compound residence section 1, and a space between an external cylinder constituted by the reactor 8 and the internal cylinder 9 functions as the activation substance circulation section 2. In this apparatus, the activation substance and the reaction compound flow in parallel.

Figure 4:
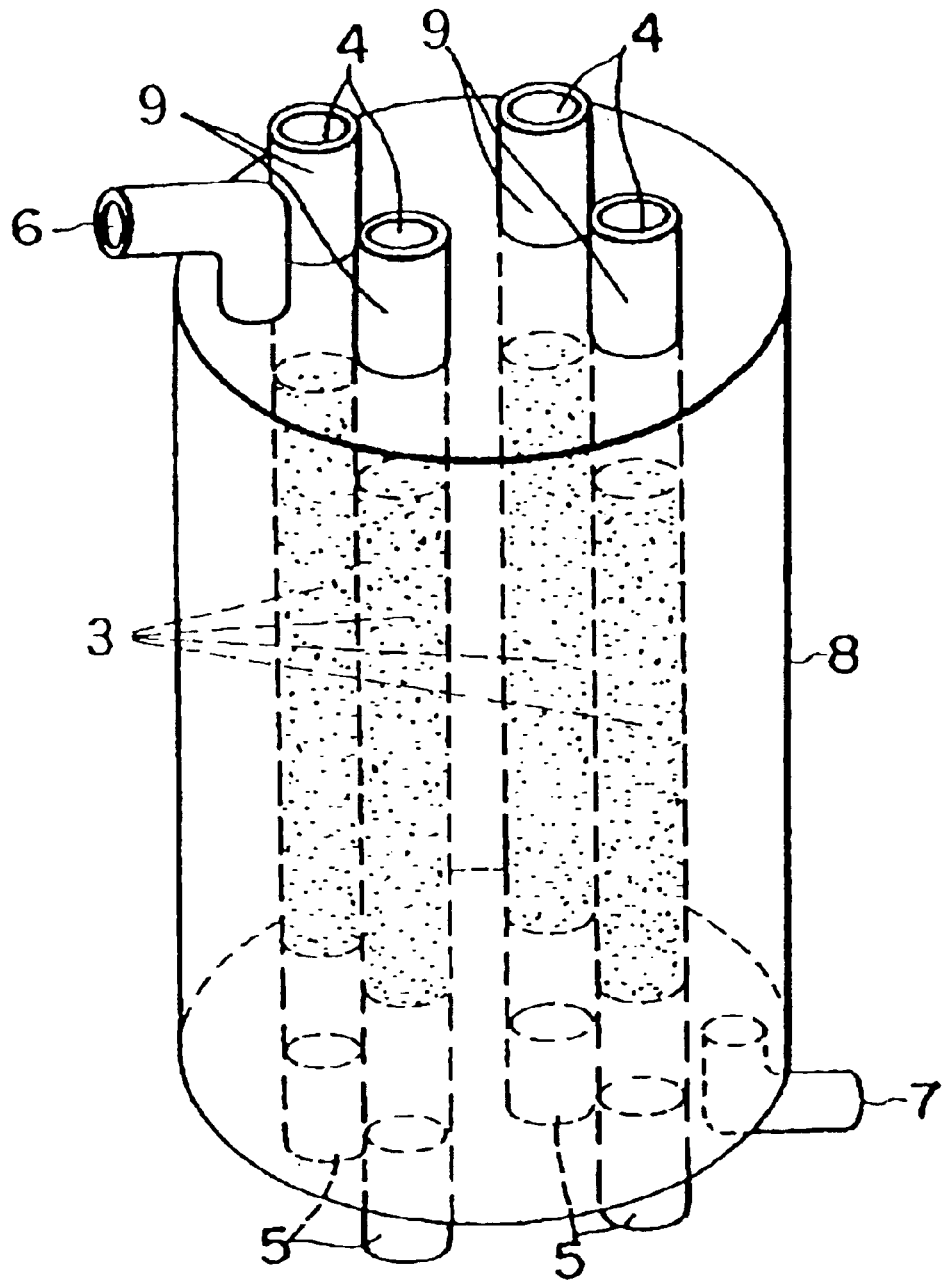
FIG. 4 is an oblique view showing yet another embodiment of the diaphragm type catalyst reaction apparatus of the present invention.

FIG. 4 is a view showing yet another reaction apparatus of the present invention comprising a plurality of the internal cylinders 9 as in FIG. 3. Since the reaction apparatus of this structure utilizes a plurality of the cylindrical diaphragm type catalysts 3, the area of the diaphragm type catalysts 3 involved in the reaction can be increased.

Figure 5:
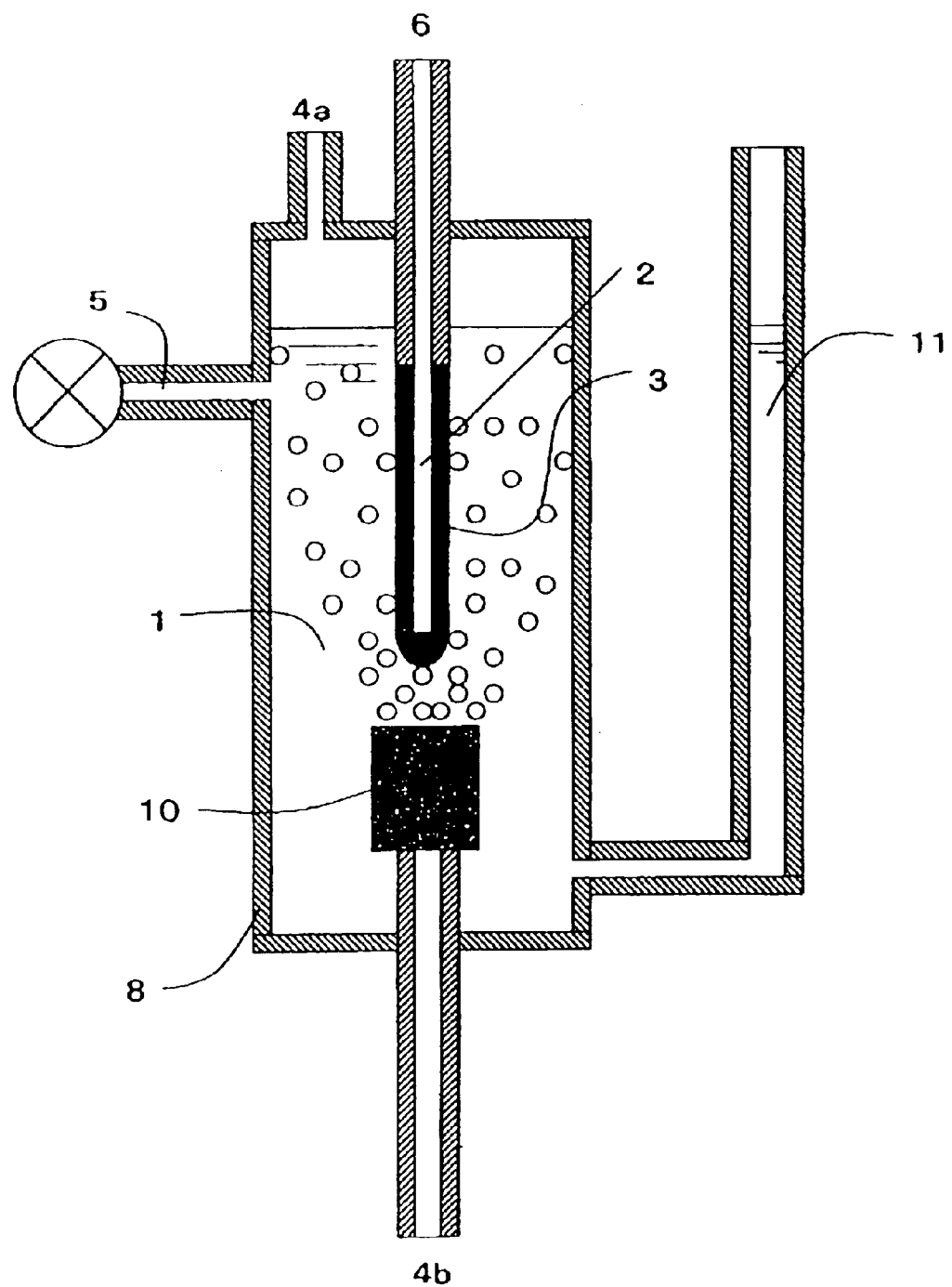
FIG. 5 is a cross-sectional view schematically showing a further embodiment of the diaphragm type catalyst reaction apparatus of the present invention.

FIG. 5 is a longitudinal sectional view showing a dual-pipe reactor for liquid phase reaction. In FIG. 5, 1, 5, 6, and 8 indicate the same as above, 10 indicates a gas volatilization apparatus (bubbler), and 11 indicates a level gauge.

In this apparatus, a reaction compound such as an aromatic hydrocarbon is introduced into the reaction compound residence section 1 from a reaction compound inlet port 4a. Another reaction compound such as oxygen is introduced into the reaction compound residence section 1 via a reaction compound inlet port 4b and the gas volatilization apparatus 10. Furthermore, activated hydrogen is introduced into the reaction compound residence section 1 via the diaphragm type catalyst 3 from the activation substance inlet port 6. In this reaction compound residence section 1, the activated hydrogen is reacted with oxygen and an aromatic hydrocarbon to produce an aromatic alcohol. The resulting aromatic alcohol is removed from the reaction compound outlet port 5.

If an aromatic hydrocarbon is not used and oxygen from the reaction compound inlet port 4b is reacted with hydrogen from the activation substance inlet port 6, while using water as a solvent, hydrogen peroxide can be obtained. The aqueous solution containing hydrogen peroxide is removed from the reaction compound outlet port 5 or the like.

This suggests the possibility of a reaction mechanism, in which hydrogen activated by the diaphragm type catalyst 3 is reacted with oxygen to produce hydrogen peroxide and then the hydrogen peroxide is further reacted with an aromatic hydrocarbon.

The reaction apparatuses used in the present invention are as illustrated above. A heating or cooling apparatus which covers the reaction apparatus, an instrument for measuring internal temperature or pressure, and the like are omitted in the illustration. However, it is needless to mention that this apparatus or instrument should be optionally added.

To obtain a reaction product by the reaction using the above diaphragm type catalyst reaction apparatus, it is important to cause a gaseous component involved in the reaction, especially oxygen or hydrogen, to be activated while permeating from one side to the other through the diaphragm type catalyst.

Illustrating this requirement by way of the embodiment shown in FIG. 1, if a raw material hydrocarbon and oxygen are respectively introduced from the reaction compound inlet port 4 and the activation substance inlet port 6, oxygen permeating through the diaphragm type catalyst 3 produces oxygen species by being activated by the catalytically active component on the surface of the catalyst as well as on the surface of pores in the catalyst. Oxidation reaction proceeds by reacting the oxygen species with a hydrocarbon in the reaction compound residence section 1.

If a raw material hydrocarbon and oxygen are introduced from the reaction compound inlet port 4 and hydrogen is introduced from the activation substance inlet port 6, hydrogen permeating through the diaphragm type catalyst is activated by the catalytically active component on the surface of the catalyst as well as on the surface of pores in the catalyst. Oxidation reaction proceeds by using hydrogen to produce activated oxygen species from oxygen in a gas phase. The resulting product is collected from the reaction compound outlet port 5.

A pressure controller or flow rate controller may be optionally installed at the activation substance outlet port 7. This enables the amount of permeation of oxygen supplied from the activation substance inlet port 6 into the reaction compound residence section 1 to be controlled. The total amount of oxygen supplied may be allowed to permeate into the reaction compound residence section 1 by closing the activation substance outlet port 7. A pressure controller or flow controller may be installed at the reaction compound outlet port 5. This enables control of the amount of permeation of hydrocarbon gas supplied from the reaction compound inlet port 4 to the activation substance circulation section 2. The total amount of hydrocarbon gas supplied may be allowed to permeate into the activation substance circulation section 2 by closing the reaction compound outlet port 5. In order to improve catalytic effects of the diaphragm type catalyst 3 on the raw material gas, a filler may be provided or an obstructive board or the like may be installed in the reaction compound residence section 1 or the activation substance circulation section 2 to change the state of gas flow.

Oxidation reaction conditions when the apparatus of the present invention is used vary according to the type of reaction. The reaction temperature is in the range of $-200°$ C. to $900°$ C., and preferably $0°$ C. to $600°$ C. The reaction pressure is in the range of $0.1-100$ kg/cm$^2$, and preferably $0.5-50$ kg/cm$^2$.

Preferable raw material hydrocarbons for oxidation reaction of the first embodiment reaction of the present invention using the diaphragm type catalyst reaction apparatus of the present invention include paraffins having 1–8 carbon atoms, olefins having 2–12 carbon atoms, and aromatic compounds having 6–20 carbon atoms.

Reaction conditions when an aromatic alcohol is produced from hydrogen gas, an aromatic hydrocarbon, and oxygen by the second embodiment reaction of the present invention vary according to the type of aromatic hydrocarbon or catalyst. The reaction temperature is in the range of $-200°$ C. to $900°$ C., and preferably $-10°$ C. to $600°$ C. The reaction pressure is in the range of $0.1-150$ kg/cm$^2$, and preferably $0.5-50$ kg/cm$^2$.

The main raw material used in the second embodiment reaction of the present invention is an aromatic hydrocarbon selected from carbocyclic compounds and heterocyclic compounds having at least one aromatic ring. As the carbocyclic compound having at least one aromatic ring, a monocyclic, dicyclic, or tricyclic aromatic compound, or a nuclear-substituted derivative of said compound is used.

The monocyclic aromatic compound is benzene or a nuclear-substituted derivative of benzene of the following formula:

wherein Ar represents a benzene ring, X, which may be the same or different when n is two or more, represents a group on an aromatic ring selected from alkyl groups having 1–24 carbon atoms, amino groups, hydroxyl groups, carboxyl groups, ester groups, cyano groups, nitro groups, halogen atoms, and oxygen, and n is an integer of 1–5.

The dicyclic aromatic compound is, for example, naphthalene, tetralin, biphenyl, cyclohexylbenzene, indan, or a nuclear-substituted derivative of these compounds of which the nucleus is substituted with a substituent represented by X in the above formula (I).

The tricyclic aromatic compound is anthracene, phenanthrene, fluorene, azulene, or a nuclear-substituted derivative of these compounds of which the nucleus is substituted with a substituent represented by X in the above formula (I), for example.

The heterocyclic compound having at least one aromatic ring is, for example, pyrane, furan, thiophene, terthiophene, pyrrole, pyridine, terpyridine, pyridine oxide, pyrazine, indole, quinoline, purine, quinazoline, bipyridine, phenanthroline, or a nuclear-substituted derivative of these compounds of which the nucleus is substituted with a substituent represented by X in the above formula (I).

If the oxidation reaction of the first embodiment reaction is conducted using the above diaphragm type catalyst reaction apparatus of the present invention, reaction gas concentration can be increased. As a result, a reaction rate equal to or more than that of the conventional catalytic reaction can be realized. Furthermore, since gaseous materials involved in the oxidation reaction can be easily controlled to have a contact minimally required for the reaction with each other by controlling the amount of gas permeating through the diaphragm, an overreaction can be prevented, and the explosion risk is significantly reduced.

Since an oxygen-containing organic compound produced on one surface of the diaphragm is ceaselessly swept or expelled from the diaphragm by the action of a raw material hydrocarbon or diluent, successive oxidation of the oxygen-containing organic compound is prevented. This contributes to a high selectivity, resulting in a high yield.

According to the second embodiment reaction, an aromatic alcohol can be easily produced at a high yield by reacting an aromatic hydrocarbon and oxygen as raw materials with activated hydrogen.

EXAMPLES

The present invention will be described in more detail by way of examples and reference example, which should not be construed as limiting the present invention.

Reference Example 1
(Production of Diaphragm Type Catalyst)

A tube used as a porous membrane was produced according to the method described in Example 1 of Japanese Patent No. 1850556. Specifically, a porous α-alumina tube having an external diameter of about 2.0 mm, internal diameter of about 1.6 mm, and pore diameter of 0.2 μm was produced using α-alumina powder with a particle diameter of 0.3 μm. Using a mercury porosimetry, the tube was measured to have a specific area of 6 m$^2$/g and a porosity of 43 vol %.

Then, according to the example described in Japanese Patent Application Laid-open No. 11-300182, palladium was carried on the produced porous membrane using a CVD method. The resulting porous membrane carrying palladium has a thickness of the palladium metal layer of 1 μm and a content of the carried palladium metal of 2.0 wt %.

Example 1

Using the porous membrane carrying palladium produced in Reference Example 1 as a diaphragm type catalyst and a reaction apparatus of the same type as shown in FIG. 3, an oxidation reaction of propylene was conducted as follows. Propylene, oxygen, and nitrogen were supplied to a reaction compound residence section 1 respectively at a rate of 0.04 mmol/min, 0.21 mmol/min, and 0.58 mmol/min. Hydrogen and nitrogen were supplied to an activation substance circulation section 2 respectively at a rate of 0.08 mmol/min and 1.58 mmol/min. The reaction was conducted at 200° C. under normal pressure (in gas circulation) to produce a product. The product was collected from an outlet port 5 in FIG. 1.

The reaction product was analyzed using a gas chromatography to confirm that the oxygen-containing organic compound was acrolein, the conversion rate from propylene was 70 mol %, and the selectivity of acrolein was 38 mol % for the raw material propylene. Therefore, the yield was 27 mol %.

Example 2

The reaction as in Example 1 was conducted except that propylene, oxygen, and nitrogen were supplied to the reaction compound residence section 1 of the apparatus of Example 1 respectively at a rate of 0.04 mmol/min, 0.06 mmol/min, and 0.73 mmol/min. The reaction product was analyzed to confirm that the oxygen-containing organic compound was acetone, the conversion rate from propylene was 28 mol %, and the selectivity of acetone was 76 mol % for the raw material propylene. Therefore, the yield was 21 mol %.

Example 3

Cyclohexene, oxygen, and nitrogen were supplied to the reaction compound residence section 1 of the apparatus of Example 1 respectively at a rate of 0.72 mmol/min, 0.36 mmol/min, and 1.8 mmol/min. Hydrogen and nitrogen were supplied to the activation substance circulation section 2 respectively at a rate of 0.36 mmol/min and 3.2 mmol/min. The reaction was conducted at 100° C. under normal pressure to produce cyclohexene oxide, cyclohexanol, cyclohexanone, and cyclohexenone as the oxygen-containing organic compounds respectively at a yield of 0.03 mol %, 0.01 mol %, 0.02 mol %, and 0.09 mol %.

This Example confirmed that cyclohexene oxide, cyclohexanol, cyclohexanone, cyclohexenone, and the like were produced using cyclohexene as a raw material.

Example 4

Using the reactor of FIG. 3 which incorporates the porous membrane carrying palladium produced in Reference Example 1 as a diaphragm type catalyst, an oxidation reaction of benzene was conducted as follows. Hydrogen gas diluted with helium to a concentration of 12.5% was introduced into the activation substance circulation section 2 from an activation substance inlet port 6. Oxygen at a concentration of 5.2% and benzene at a concentration of 1.6% were introduced into the reaction compound residence section 1 respectively at a flow rate of 25 ml/h. The reactor was heated, and the compounds in the reactor were continuously reacted at 150° C. for three hours. After the reaction, a part of the resulting gas mixture was collected and analyzed. Phenol was obtained as the main product. The conversion rate from benzene was 13.25%, and the yield of phenol was 11.3%.

Example 5

The same reaction as in Example 4 was conducted while changing oxygen and benzene concentrations as follows. Hydrogen gas diluted with helium to a concentration of 25.0% was introduced into the activation substance circulation section 2 from the activation substance inlet port 6. Oxygen at a concentration of 1.6% and benzene at a concentration of 10% were introduced into the reaction compound residence section 1 respectively at a flow rate of 35 ml/h. After the reaction at 160° C., the reaction product was collected and analyzed as in Example 4 to confirm that the main product was phenol, the conversion rate from benzene was 1.6%, and the yield of phenol was 1.54%.

Example 6

The same reaction as in Example 4 was conducted while changing oxygen and benzene concentrations. Hydrogen gas diluted with helium to a concentration of 30.0% was introduced into the activation substance circulation section 2 from the activation substance inlet port 6. Oxygen at a concentration of 25% and benzene at a concentration of 1.8% were introduced into the reaction compound residence section 1 respectively at a flow rate of 35 ml/h. After the reaction at 250° C., the reaction product was analyzed to confirm that the main product was phenol, the conversion rate from benzene was 2.05%, and the yield of phenol was 1.9%.

Example 7

The test was conducted in the same manner as in Example 4 except that the vent pipe into which hydrogen was introduced and the vent pipe into which oxygen and benzene were introduced were reverse. Specifically, hydrogen gas diluted with helium to a concentration of 10.0% was introduced into the reaction compound residence section 1 in FIG. 3. Oxygen at a concentration of 5% and benzene at a concentration of 0.8% were introduced into the activation substance circulation section 2 in FIG. 3 respectively at a flow rate of 25 ml/h. The reaction was conducted at 150° C. The main product was phenol, the conversion rate from benzene was 2.11%, and the yield of phenol was 2.00%.

Example 8

The same reaction as in Example 4 was conducted except that the reaction temperature was 200° C. After the reaction, the reaction product was analyzed to confirm that the main product was phenol, the conversion rate from benzene was 12.30%, and the yield of phenol was 11.0%.

Example 9

The same reaction as in Example 4 was conducted except that the reaction temperature was 200° C. The main product was phenol, the conversion rate from benzene was 3.00%, and the yield of phenol was 2.8%.

Example 10

The same reaction as in Example 4 was conducted except that the reaction temperature was 250° C. The main product was phenol, the conversion rate from benzene was 13.5%, and the yield of phenol was 11.5%.

Example 11

The reaction was conducted under the conditions of Example 8 for 24 hours. The gas mixture was collected and analyzed to confirm that the main product was phenol, the conversion rate from benzene was 11.30%, and the yield of phenol was 10.0%.

Example 12

The reaction was conducted under the conditions of Example 10 for 24 hours. The gas mixture was collected and analyzed to confirm that the main product was phenol, the conversion rate from benzene was 14.0%, and the yield of phenol was 12.5%.

Example 13

Using a reactor shown in FIG. 5 which incorporates the porous membrane carrying palladium produced in Reference Example 1 as a diaphragm type catalyst, liquid phase reaction was conducted as follows. 25 ml of benzene was introduced into a reaction compound residence section 1 from a reaction compound inlet port 4a. Then, oxygen and hydrogen were introduced into the above residence section 1 respectively from a reaction compound inlet port 4b and an activation substance circulation section 2. Oxygen was suitably supplied to a diaphragm type catalyst wall 3 as bubbles through a bubbler 10. The reaction was conducted at an oxygen flow rate of 5 l/h under a hydrogen pressure of 3 kg/cm$^2$ at 20° C. 24 hours after the reaction, the reaction product was analyzed to confirm that the main product was phenol, the conversion rate from benzene was 10.0%, and the yield of phenol was 8.8%.

Example 14

After the reaction of Example 13, the aromatic phase was replaced with fresh benzene to repeat the test. Specifically, 24 hours after the reaction of Example 13, oxygen and hydrogen were introduced again into 25 ml of benzene in the reaction compound residence section respectively from the reaction compound inlet port 4b and the activation substance circulation section 2. The reaction was conducted under the same conditions as in Example 13. 24 hours after the reaction, the reaction product was analyzed to confirm that the main product was phenol, the conversion rate from benzene was 9.5%, and the yield of phenol was 8.4%.

Example 15

The reaction as in Example 4 was conducted except that toluene was used instead of benzene. The reaction product was analyzed to confirm that the main product was an aromatic alcohol (cresol), the conversion rate from toluene was 42%, and the yield of the aromatic alcohol was 37%.

Example 16

The reaction as in Example 4 was conducted except that methylnaphthalene was used instead of benzene. The reaction product was analyzed to confirm that the main product was an aromatic alcohol (methylnaphthol), the conversion rate from methylnaphthalene was 12%, and the yield of the aromatic alcohol was 11%.

Example 17

The reaction as in Example 13 was conducted except that pyridine was used instead of benzene. The reaction product was analyzed to confirm that the main product was hydroxypyridine, the conversion rate from pyridine was 11.2%, and the yield of hydroxypyridine was 9.8%.

Example 18

The reaction as in Example 4 was conducted except that a diaphragm carrying a silver-palladium alloy (silver:palladium=20:80, weight ratio) was used instead of the porous membrane carrying palladium. The main product was phenol, the conversion rate from benzene was 11%, and the yield of phenol was 9.9%.

Example 19

The reaction as in Example 4 was conducted except that a diaphragm carrying a nickel-vanadium alloy (nickel:vanadium=1:15, weight ratio) was used instead of the porous membrane carrying palladium. The main product was phenol, the conversion rate from benzene was 10.5%, and the yield of phenol was 9.6%.

INDUSTRIAL APPLICABILITY

The present invention relates to a reaction comprising activating one substance involved in the reaction by causing the substance to permeate through a diaphragm type catalyst and utilizing the activated substance in one step with safety.

For example, according to a method of the present invention, if inexpensive oxygen is used as a substance to be activated while permeating through the diaphragm type catalyst and a hydrocarbon is used as the other substance, the hydrocarbon is directly oxidized to obtain an oxygen-containing organic compound such as ketone, aldehyde, carboxylic acid, or epoxide advantageously with safety.

If hydrogen is used as a substance to be activated while permeating through the diaphragm type catalyst and an aromatic hydrocarbon and oxygen are used as the other substances, an aromatic alcohol can be advantageously obtained with safety.

Furthermore, according to the method of the present invention, contact of an activated substance with a compound to be reacted with the activated substance can be freely controlled. Therefore, an overreaction of a target product can be prevented, resulting in a high production yield.

Therefore, the method of the present invention is highly economically advantageous as a method for industrial production of oxygen-containing organic compounds such as an aromatic alcohol, ketone, aldehyde, carboxylic acid, and epoxide, for example.

What is claimed is:

1. A method for producing an oxygen-containing organic compound comprising providing a reactor with a plurality of adjacent chambers partitioned by a diaphragm type catalyst that can activate a substance permeating therethrough, causing hydrogen gas to be activated by the diaphragm type catalyst to circulate in one of the chambers, causing a hydrocarbon and oxygen to be reacted with the activated hydrogen to circulate in the other chamber, activating the hydrogen while permeating through the diaphragm type catalyst, and reacting the activated hydrogen with the hydrocarbon and oxygen.

2. The method according to claim 1, wherein the diaphragm type catalyst belongs to any one of the groups (A)–(D):
  (A) a metal membrane,
  (B) an alloy membrane,
  (C) a noble metal carried on a metal oxide porous membrane, and
  (D) a transition metal oxide or lanthanide oxide carried on a metal oxide porous membrane.

3. The method according to claim 2, wherein the metal membrane (A) is formed from a metal selected from a group consisting of palladium, niobium, tantalum, and vanadium, or is formed by applying palladium to a metal membrane formed from a metal selected from a group consisting of niobium, tantalum, and vanadium.

4. The method according to claim 2, wherein the alloy membrane (B) is formed from an alloy of one or more elements selected from a group consisting of first-row transition metals, second-row transition metals, third-row transition metals, lanthanides, and actinides and a metal selected from a group consisting of palladium, niobium, tantalum, and vanadium.

5. The method according to claim 2, wherein the alloy membrane (B) is formed from an alloy of one or more elements selected from a group consisting of yttrium, cerium, silver, nickel, and titanium and a metal selected from a group consisting of palladium, niobium, tantalum, and vanadium.

6. The method according to claim 2, wherein the noble metal (C) carried on the metal oxide porous membrane is selected from a group consisting of silver, gold, platinum, and palladium.

7. The method according to claim 2, wherein the transition metal oxide (D) carried on the metal oxide porous membrane is an oxide of a transition metal selected from a group consisting of chromium, manganese, iron, cobalt, nickel, osmium, ruthenium, vanadium, molybdenum, tungsten, and bismuth.

8. The method according to claim 2, wherein the lanthanide oxide (D) carried on the metal oxide porous membrane is an oxide of an element selected from a group consisting of cerium, lanthanum, and samarium.

9. A method for producing an aromatic alcohol by reacting oxygen, hydrogen, and an aromatic hydrocarbon in one step, wherein hydrogen activated while permeating through a diaphragm type catalyst is reacted with an aromatic hydrocarbon and oxygen.

10. The method according to claim 9, wherein the reaction is conducted in a reactor partitioned by a diaphragm type catalyst into a plurality of adjacent chambers, one of the chambers being designed to cause hydrogen to circulate and the other chamber being designed to cause an aromatic hydrocarbon and oxygen to circulate, wherein hydrogen is activated while permeating through the diaphragm type catalyst and the activated hydrogen is reacted with the aromatic hydrocarbon and oxygen.

11. The method according to claim 10, wherein one diaphragm type catalyst partitions the reactor into two chambers.

12. The method according to claim 9, wherein the diaphragm type catalyst belongs to any one of the groups (A)–(D):
(A) a metal membrane,
(B) an alloy membrane,
(C) a noble metal carried on a metal oxide porous membrane, and
(D) a transition metal oxide or lanthanide oxide carried on a metal oxide porous membrane.

13. The method according to claim 12, wherein the metal membrane (A) is formed from a metal selected from a group consisting of palladium, niobium, tantalum, and vanadium, or is formed by applying palladium to a metal membrane formed from a metal selected from a group consisting of niobium, tantalum, and vanadium.

14. The method according to claim 12, wherein the alloy membrane (B) is formed from an alloy of one or more elements selected from a group consisting of first-row transition metals, second-row transition metals, third-row transition metals, lanthanides, and actinides and a metal selected from a group consisting of palladium, niobium, tantalum, and vanadium.

15. The method according to claim 14, wherein the alloy membrane (B) is formed from an alloy of one or more elements selected from a group consisting of yttrium, cerium, silver, nickel, and titanium and a metal selected from a group consisting of palladium, niobium, tantalum, and vanadium.

16. The method according to claim 14, wherein the noble metal (C) carried on the metal oxide porous membrane is selected from a group consisting of silver, gold, platinum, and palladium.

17. The method according to claim 14, wherein the transition metal oxide (D) carried on the metal oxide porous membrane is an oxide of a transition metal selected from a group consisting of chromium, manganese, iron, cobalt, nickel, osmium, ruthenium, vanadium, molybdenum, tungsten, and bismuth.

18. The method according to claim 14, wherein the lanthanide oxide (D) carried on the metal oxide porous membrane is an oxide of an element selected from a group consisting of cerium, lanthanum, and samarium.

19. The method according to claim 14, wherein the metal oxide porous membrane is a porous membrane of a metal oxide selected from a group consisting of silica, alumina, titania, and zirconia, a porous membrane of a composite material formed from two or more of these four metal oxides, or a porous membrane of zeolite.

20. The method according to claim 9, wherein oxygen is pure oxygen gas, ozone gas, a mixture of the pure oxygen gas and ozone gas, or a solution of one or more of these gases.

21. The method according to claim 9, wherein the aromatic hydrocarbon is a carbocyclic compound or heterocyclic compound having at least one aromatic ring.

22. The method according to claim 21, wherein the carbocyclic compound having at least one aromatic ring is a monocyclic, dicyclic, or tricyclic aromatic compound, or a nuclear-substituted derivative of said compound.

23. The method according to claim 21, wherein the monocyclic aromatic compound is benzene or a nuclear-substituted derivative of benzene of the following formula:

$$\mathrm{Ar{-}X_n} \qquad (I)$$

wherein Ar represents a benzene ring, X individually represents a group selected from alkyl groups having 1–24 carbon atoms, amino groups, hydroxyl groups, carboxyl groups, ester groups, cyano groups, nitro groups, halogen atom, and oxygen, and n is an integer of 1–5.

24. The method according to claim 21, wherein the dicyclic aromatic compound is naphthalene, tetralin, biphenyl, cyclohexylbenzene, indan, or a nuclear-substituted derivative of these compounds of which the nucleus is substituted with a substituent represented by X in the above formula (I).

25. The method according to claim 21, wherein the tricyclic aromatic compound is anthracene, phenanthrene, fluorene, azulene, or a nuclear-substituted derivative of these compounds of which the nucleus is substituted with a substituent represented by X in the above formula (I).

26. The method according to claim 21, wherein the heterocyclic compound having at least one aromatic ring is pyrane, furan, thiophene, terthiophene, pyrrole, pyridine, terpyridine, pyridine oxide, pyrazine, indole, quinoline, purine, quinazoline, bipyridine, phenanthroline, or a nuclear-substituted derivative of these compounds of which the nucleus is substituted with a substituent represented by X in the above formula (I).

27. The method according to claim 6, wherein the metal oxide porous membrane is a porous membrane of a metal oxide selected from a group consisting of silica, alumina, titania, and zirconia, a porous membrane of a composite material formed from two or more of these four metal oxides, or a porous membrane of zeolite.

28. The method according to claim 7, wherein the metal oxide porous membrane is a porous membrane of a metal oxide selected from a group consisting of silica, alumina, titania, and zirconia, a porous membrane of a composite material formed from two or more of these four metal oxides, or a porous membrane of zeolite.

29. The method according to claim 8, wherein the metal oxide porous membrane is a porous membrane of a metal oxide selected from a group consisting of silica, alumina, titania, and zirconia, a porous membrane of a composite material formed from two or more of these four metal oxides, or a porous membrane of zeolite.

* * * * *